United States Patent [19]

Riebli

[11] Patent Number: 5,010,082
[45] Date of Patent: Apr. 23, 1991

[54] PESTICIDAL 2-HYDRAZINOPYRAMIDINE COMPOUNDS

[75] Inventor: Peter Riebli, Buckten, Switzerland

[73] Assignee: Ciba-Geigy Corporation, Ardsley, N.Y.

[21] Appl. No.: 411,337

[22] Filed: Sep. 22, 1989

[30] Foreign Application Priority Data

Sep. 28, 1988 [CH] Switzerland ............ 3595/88

[51] Int. Cl.$^5$ ............ C07D 239/46; C07D 239/48; A01N 43/54
[52] U.S. Cl. ............ 514/272; 514/275; 544/320; 544/321; 544/330; 544/332
[58] Field of Search ............ 544/321, 332, 330; 514/272, 275

[56] References Cited

FOREIGN PATENT DOCUMENTS 019450 11/1980 European Pat. Off. ............ 544/330

Primary Examiner—Mukund J. Shah
Assistant Examiner—Phil Datlow
Attorney, Agent, or Firm—George R. Dohmann; Edward McC. Roberts

[57] ABSTRACT

Compounds of formula

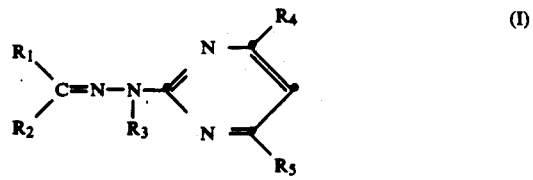

wherein: $R_1$ is phenyl, naphthyl, phenyl substituted from one to five times by $R_6$, or naphthyl substituted from one to five times by $R_6$; $R_2$ is $C_1$-$C_6$alkyl, $C_1$-$C_6$alkyl substituted at least once by halogen, $C_1$-$C_3$alkoxy and/or by $C_3$-$C_6$cycloalkyl, $C_3$-$C_6$cycloalkyl, $C_1$-$C_4$alkoxycarbonyl, phenyl, phenyl mono- to tri-substituted by halogen, $C_1$-$C_3$alkoxy and/or by $C_1$-$C_3$alkyl, benzyl, or benzyl mono- to tri-substituted by halogen, $C_1$-$C_3$alkoxy and/or by $C_1$-$C_3$alkyl; $R_3$ is hydrogen, $C_1$-$C_6$alkyl or the radical CO-$R_7$; $R_4$ is $C_3$-$C_6$cycloalkyl, $C_3$-$C_6$cycloalkyl mono- to tri-substituted by halogen and/or by methyl, $C_1$-$C_4$alkyl substituted at least once by halogen, hydroxy and/or by cyano, $C_2$-$C_5$alkynyl, $C_1$-$C_4$alkylthio or the radical $CH_2XR_8$; $R_5$ is hydrogen, $C_1$-$C_6$alkyl, $C_1$-$C_6$alkyl substituted at least once by halogen, hydroxy, cyano and/or by $C_1$-$C_3$alkoxy, $R_5$ is also $C_3$-$C_5$alkenyl, halogen, hydroxy, $C_1$-$C_3$alkoxy, $C_1$-$C_3$haloalkoxy, $C_3$-$C_6$cycloalkyl or $C_1$-$C_3$alkylthio; $R_6$, independently of any other, is $C_1$-$C_6$alkyl, $C_1$-$C_3$alkyl substituted by $C_1$-$C_3$alkoxy, or $C_1$-$C_4$alkoxy, $C_1$-$C_3$haloalkyl, $C_1$-$C_3$haloalkoxy, halogen, cyano, nitro, hydroxy or the radical $S(O)_n$-$C_1$-$C_4$alkyl; $R_7$ is $C_1$-$C_6$alkyl, or $C_1$-$C_6$alkyl substituted at least once by halogen and/or by $C_1$-$C_3$alkoxy; $R_8$ is $C_1$-$C_6$alkyl, $C_1$-$C_6$alkyl substituted at least once by halogen, hydroxy, cyano and/or by $C_1$-$C_4$alkoxy, $C_3$-$C_6$alkenyl, $C_3$-$C_6$alkynyl or $C_3$-$C_6$cycloalkyl; X is oxygen or sulfur; and n is 0, 1 or 2; including the acid addition compounds and the metal salt complexes thereof, have valuable microbicidal properties. The novel compounds can be used in plant protection for preventing attacks on cultivated plants by phytopathogenic microorganisms and for controlling those microorganisms.

21 Claims, No Drawings

PESTICIDAL 2-HYDRAZINOPYRIMIDINE COMPOUNDS

The present invention relates to novel 2-hydrazinopyrimidine derivatives of formula I below. The invention relates also to the preparation of those compounds and to agrochemical compositions that contain at least one of those compounds as active ingredient. The invention relates also to the preparation of the said compositions and to the use of the compounds or the compositions for controlling pests, especially plant-destructive microorganisms, particularly fungi.

The compounds according to the invention have the general formula I

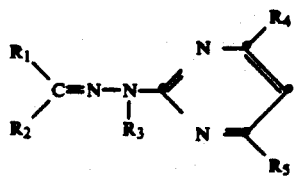

wherein $R_1$ is phenyl, naphthyl, phenyl substituted from one to five times by $R_6$, or naphthyl substituted from one to five times by $R_6$; $R_2$ is $C_1$-$C_6$alkyl, $C_1$-$C_6$alkyl substituted at least once by halogen, $C_1$-$C_3$alkoxy and/or by $C_3$-$C_6$cycloalkyl, $C_3$-$C_6$cycloalkyl, $C_1$-$C_4$alkoxycarbonyl, phenyl, phenyl mono- to tri-substituted by halogen, $C_1$-$C_3$alkoxy and/or by $C_1$-$C_3$alkyl, benzyl, or benzyl mono- to tri-substituted by halogen, $C_1$-$C_3$alkoxy and/or by $C_1$-$C_3$alkyl; $R_3$ is hydrogen, $C_1$-$C_6$alkyl or the radical CO-$R_7$; $R_4$ is $C_3$-$C_6$cycloalkyl, $C_3$-$C_6$cycloalkyl mono- to tri-substituted by halogen and/or by methyl, $C_1$-$C_4$alkyl substituted at least once by halogen, hydroxy and/or by cyano, $C_2$-$C_5$alkynyl, $C_1$-$C_4$alkylthio or the radical $CH_2XR_8$; $R_5$ is hydrogen, $C_1$-$C_6$alkyl, $C_1$-$C_6$alkyl substituted at least once by halogen, hydroxy, cyano and/or by $C_1$-$C_3$alkoxy, $R_5$ is also $C_3$-$C_5$alkenyl, halogen, hydroxy, $C_1$-$C_3$alkoxy, $C_1$-$C_3$haloalkoxy, $C_3$-$C_6$-cycloalkyl or $C_1$-$C_3$alkylthio; $R_6$, independently of any other, is $C_1$-$C_6$-alkyl, $C_1$-$C_3$alkyl substituted by $C_1$-$C_3$alkoxy, or $C_1$-$C_4$alkoxy, $C_1$-$C_3$haloalkyl, $C_1$-$C_3$haloalkoxy, halogen, cyano, nitro, hydroxy or the radical $S(O)_n$-$C_1$-$C_4$alkyl; $R_7$ is $C_1$-$C_6$alkyl, or $C_1$-$C_6$alkyl substituted at least once by halogen and/or by $C_1$-$C_3$alkoxy; $R_8$ is $C_1$-$C_6$alkyl, $C_1$-$C_6$alkyl substituted at least once by halogen, hydroxy, cyano and/or by $C_1$-$C_4$alkoxy, $C_3$-$C_6$alkenyl, $C_3$-$C_6$alkynyl or $C_3$-$C_6$cycloalkyl; X is oxygen or sulfur; and n is 0, 1 or 2; including the acid addition compounds and the metal salt complexes thereof.

Depending upon the number of carbon atoms indicated, "alkyl" by itself or as a constituent of another substituent, such as haloalkyl, alkoxy or haloalkoxy, is to be understood as being, for example, methyl, ethyl, propyl, butyl, pentyl and hexyl and the isomers thereof, for example isopropyl, isobutyl, tert.-butyl or sec.-butyl. Halogen, also called Hal, is fluorine, chlorine, bromine or iodine. Haloalkyl and haloalkoxy are mono- to perhalogenated radicals, for example $CHCl_2$, $CH_2F$, $CCl_3$, $CH_2Cl$, $CHF_2$, $CF_3$, $CH_2CH_2Br$, $C_2Cl_5$, $CHBr$, $CHBrCl$, etc., preferably $CF_3$. Depending upon the number of carbon atoms indicated, cycloalkyl is, for example, cyclopropyl, cyclobutyl, cyclopentyl or cyclohexyl.

The compounds of formula I are oils, resins or solids that are stable at room temperature and are distinguished by valuable microbicidal properties. They can be used preventively and curatively in the agricultural sector or related fields for controlling plant-destructive microorganisms. The compounds of formula I according to the invention are, when used in low concentrations, distinguished not only by excellent fungicidal activity but also by particularly good plant compatability.

The invention relates both to the free compounds of formula I and to their addition salts with inorganic and organic acids and to the metal salt complexes of formula I.

Salts according to the invention are especially addition salts with non-harmful inorganic acids, for example hydrohalic acids, for example hydrochloric, hydrobromic or hydriodic acid, or sulfuric acid, phosphoric acid, phosphorous acid, nitric acid, or with organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1.2-naphthalene-disulfonic acid.

Metal salt complexes of formula I according to the invention comprise the fundamental organic molecule and an inorganic or organic metal salt, for example the halides, nitrates, sulfates, phosphates, acetates, trifluoroacetates, trichloroacetates, propionates, tartrates, sulfonates, salicylates, benzoates, etc., of the elements of the second main group, such as calcium and magnesium, and of the third and fourth main groups, such as aluminum, tin or lead, and of the first to eighth sub-groups, such as chromium, manganese, iron, cobalt, nickel, copper, zinc etc. Sub-group elements of the 4th period are preferred. The metals may be present in any of the various valencies attributed to them. The metal complexes may be mononuclear or polynuclear, that is to say they may contain one or more organic molecular components as ligands.

As a result of the C=N double bond, two stereoisomeric forms of the compounds of formula I exist, namely the E-form and a Z-form. During the preparation of these compounds generally a mixture of the two isomers is formed. The ratio in which they are formed depends upon several conditions; for example, upon the structure of the starting material, the nature of the reaction medium, its pH value, the reaction conditions, such as temperature and duration and any catalyst used. By providing certain conditions it is possible to synthesis a single isomer in pure form. If a mixture of isomers is obtained, the pure components can be isolated in various ways, for example by column-chromatographic separation methods. The identification of the isomers is usually effected by NMR spectroscopic analyses, the "chemical shift" of the proton resonance signal in the NH group being determined in the case of the compounds of formula I. The compounds of formula I can be converted into their tautomeric forms under the action of heat and radiation by light.

In respect of the compounds of formula I the present invention includes all pure isomers and mixtures thereof. The following groups of compounds of formula I are preferred owing to their pronounced microbicidal, especially phytofungicidal, activity:

Group 1: Compounds of formula I wherein: $R_1$ is phenyl, naphthyl, phenyl substituted up to five times by $R_6$, or naphthyl substituted up to five times by $R_6$; $R_2$ is $C_1-C_6$alkyl, $C_1-C_6$alkyl substituted from one to five times by halogen or once or twice by $C_1-C_3$alkoxy and/or once by $C_3-C_6$cycloalkyl, $C_3-C_6$cycloalkyl, phenyl, phenyl mono- to tri-substituted by halogen, $C_1-C_3$alkoxy and/or by $C_1-C_3$alkyl, benzyl, or benzyl mono- to tri-substituted by halogen, $C_1-C_3$alkoxy and/or by $C_1-C_3$alkyl; $R_3$ is hydrogen, $C_1-C_3$alkyl or the radical $CO-R_7$; $R_4$ is $C_3-C_6$cycloalkyl, $C_3-C_6$cycloalkyl mono- to tri-substituted by halogen and/or by methyl, $C_1-C_4$alkyl substituted at least once by halogen, hydroxy and/or by cyano, $C_2-C_5$alkynyl, $C_1-C_4$alkylthio or the radical $CH_2XR_8$; $R_5$ is hydrogen, $C_1-C_6$alkyl, $C_1-C_6$alkyl substituted at least once by halogen, hydroxy, cyano and/or by $C_1-C_3$alkoxy, $R_5$ is also $C_3-C_5$alkenyl, halogen, hydroxy, $C_1-C_3$alkoxy, $C_1-C_3$haloalkoxy, $C_3-C_6$cycloalkyl or $C_1-C_3$alkylthio; $R_6$, independently of any other, is $C_1-C_4$alkyl, $C_1-C_3$alkoxy, $C_1-C_3$haloalkyl, $C_1-C_3$haloalkoxy, halogen, nitro or the radical $S(O)_n-C_1-C_3$alkyl; $R_7$ is $C_1-C_6$alkyl, or $C_1-C_6$alkyl substituted at least once by halogen and/or by $C_1-C_3$alkoxy; $R_8$ is $C_1-C_6$alkyl, $C_1-C_6$alkyl substituted at least once by halogen, hydroxy and/or by $C_1-C_4$alkoxy, $C_3-C_6$alkenyl, $C_3-C_6$alkynyl or $C_3-C_6$cycloalkyl; X is oxygen or sulfur; and n is 0, 1 or 2.

Group 2: Compounds of formula I wherein: $R_1$ is phenyl, naphthyl, phenyl substituted up to 5 times by $R_6$, or naphthyl substituted up to 3 times by $R_6$; $R_2$ is $C_1-C_6$alkyl, $C_1-C_6$alkyl substituted from 1 to 5 times by halogen or once or twice by $C_1-C_3$alkoxy and/or once by $C_3-C_6$cycloalkyl, $C_3-C_6$cycloalkyl, phenyl, phenyl mono- to tri-substituted by halogen, $C_1-C_3$alkoxy and/or by $C_1-C_3$alkyl, benzyl, or benzyl mono- to tri-substituted by halogen, $C_1-C_3$alkoxy and/or by $C_1-C_3$alkyl; $R_3$ is hydrogen, $C_1-C_3$alkyl or the radical $CO-R_7$; $R_4$ is $C_3-C_6$cycloalkyl, $C_3-C_6$cycloalkyl mono- to tri-substituted by halogen and/or by methyl, $C_2-C_5$alkynyl, $C_1-C_4$alkylthio or the radical $CH_2XR_8$; $R_5$ is hydrogen, $C_1-C_6$alkyl, $C_1-C_6$alkyl substituted at least once by halogen, hydroxy, cyano and/or by $C_1-C_3$alkoxy, $R_5$ is also $C_3-C_5$alkenyl, halogen, hydroxy, $C_1-C_3$alkoxy, $C_1-C_3$haloalkoxy, $C_3-C_6$cycloalkyl or $C_1-C_3$alkylthio; $R_6$, independently of any other, is $C_1-C_4$alkyl, $C_1-C_3$alkoxy, $C_1-C_3$haloalkyl, $C_1-C_3$haloalkoxy, halogen, nitro or the radical $S(O)_n-C_1-C_3$alkyl; $R_7$ is $C_1-C_6$alkyl, or $C_1-C_6$alkyl substituted at least once by halogen and/or by $C_1-C_3$alkoxy; $R_8$ is $C_1-C_6$alkyl, $C_1-C_6$alkyl substituted at least once by halogen, hydroxy and/or by $C_1-C_4$alkoxy, $C_3-C_6$alkenyl, $C_3-C_6$alkynyl or $C_3-C_6$cycloalkyl; X is oxygen or sulfur; and n is 0, 1 or 2.

Group 3: Compounds of formula I wherein: $R_1$ is phenyl, naphthyl, phenyl substituted up to 3 times by $R_6$, or naphthyl substituted up to 3 times by $R_6$; $R_2$ is $C_1-C_6$alkyl, $C_1-C_6$alkyl monosubstituted by $C_1-C_3$alkoxy or $C_3-C_6$cycloalkyl, and/or mono- to tri-substituted by halogen, or $C_3-C_6$cycloalkyl, phenyl, phenyl mono- to tri-substituted by halogen and/or by $C_1-C_3$alkyl, benzyl, or benzyl mono- to tri-substituted by halogen and/or by $C_1-C_3$alkyl; $R_3$ is hydrogen or the radical $CO-R_7$; $R_4$ is $C_3-C_6$cycloalkyl, $C_3-C_6$cycloalkyl mono- to tri-substituted by halogen and/or by methyl, $C_2-C_5$alkynyl, $C_1-C_4$alkylthio or the radical $CH_2XR_8$; $R_5$ is $C_1-C_6$alkyl, $C_1-C_6$alkyl substituted by hydroxy or $C_1-C_3$alkoxy and/or at least once by halogen, $R_5$ is also $C_3-C_5$alkenyl, halogen, hydroxy, $C_1-C_3$alkoxy, $C_1-C_3$haloalkoxy, $C_3-C_6$cycloalkyl or $C_1-C_3$alkylthio; $R_6$, independently of any other, is $C_1-C_4$alkyl, $C_1-C_2$alkoxy, $C_1-C_2$haloalkoxy or halogen; $R_7$ is $C_1-C_4$alkyl, or $C_1-C_4$alkyl substituted at least once by halogen; $R_8$ is $C_1-C_6$alkyl, or $C_1-C_6$alkyl substituted at least once by halogen or by $C_1-C_4$alkoxy; and X is oxygen.

Group 4: Compounds of formula I wherein: $R_1$ is phenyl substituted up to 3 times by $R_6$ with the proviso that at least the ortho-position in the phenyl ring is substituted; $R_2$ is $C_1-C_3$alkyl; $R_3$ is hydrogen; $R_4$ is $C_3-C_6$cycloalkyl, $C_3-C_6$cycloalkyl substituted by $CH_3$, or $C_2-C_4$alkynyl, $C_1-C_3$alkylthio or the radical $CH_2X-R_8$; $R_5$ is $C_1-C_3$alkyl, $C_1-C_3$alkyl substituted by halogen, $R_5$ is also $C_3-C_5$alkenyl, $C_3-C_5$cycloalkyl or $C_1-C_3$alkylthio; $R_6$, independently of any other, is $C_1-C_4$alkyl, halogen or $C_1-C_4$haloalkyl; $R_8$ is $C_1-C_3$alkyl; and X is oxygen.

An important group of phytofungicidal active ingredients according to the invention are those compounds of formula I in which the phenyl radicals of $R_1$ and $R_2$ are ortho-substituted.

Group 5: Compounds of formula I wherein: $R_1$ is α-naphthyl, 2-substituted α-naphthyl, 2,3-disubstituted or 2,4-disubstituted α-naphthyl, wherein the substituents in the 2- and 4-positions can be $C_1-C_3$alkyl, halogen or nitro and the substituent in the 3-position is $C_1-C_3$alkyl; $R_2$ is $C_1-C_3$alkyl; $R_3$ is hydrogen; $R_4$ is $C_3-C_6$cycloalkyl, $C_3-C_6$cycloalkyl substituted by $CH_3$, or $C_2-C_4$alkynyl, $C_1-C_3$alkylthio or the radical $CH_2X-R_8$; $R_5$ is $C_1-C_3$alkyl, $C_1-C_3$alkyl substituted by halogen, $R_5$ is also $C_3-C_5$alkenyl, $C_3-C_5$cycloalkyl or $C_1-C_3$alkylthio; $R_8$ is $C_1-C_3$alkyl; and X is oxygen.

Group 6: Compounds of formula I according to Group 5 wherein $R_1$ is α-naphthyl, 2-methyl-α-naphthyl, 2-methyl-4-nitro-α-naphthyl, 2,4-dimethyl-α-naphthyl, 2,3-dimethyl-α-naphthyl or 4-methyl-α-naphthyl and the remaining substituents are as defined for Group 5.

The following preferred compounds of formula I may be mentioned: 4-methyl-6-cyclopropyl-2-[1-(2-methylphenyl)-ethylidenehydrazino]pyrimidine (Compound No. 1.1); 4-methyl-6-methoxymethyl-2-[1-(2-methylphenyl)-ethylidenehydrazino]-pyrimidine (Compound No. 1.11); 4-methyl-6-cyclopropyl-2-[1-(2-chlorophenyl)-ethylidenehydrazino]-pyrimidine (Compound No. 1.13); 4-methyl-6-(1-propynyl)-2-[1-(2-methylphenyl) ethylidenehydrazino]-pyrimidine (Compound No. 1.37); 4-methyl-6-(1-propynyl)-2-[1-(2-chlorophenyl)-ethylidenehydrazino]-pyrimidine (Compound No. 1.42); 4-fluoromethyl-6-cyclopropyl-2-[1-(2-methylphenyl)-ethylidenehydrazino]-pyrimidine (Compound No. 1.53); 4-methyl-6-fluoromethyl-2-[1-(2-methylphenyl) -ethylidenehydrazino]-pyrimidine (Compound No. 1.4); 4-methyl-6-cyclopropyl-2-[1-(2,4-dimethylphenyl)-ethylidenehydrazino]pyrimidine (Compound No. 1.2); 4-methyl-6-cyclopropyl-2-[1-(2-methyl-α-naphthyl)-ethylidenehydrazino]-pyrimidine (Compound No. 3.25); 4-methyl-6-cyclopropyl-2-[1-(2,4-dimethyl-α-naphthyl)-ethylidenehydrazino]-pyrimidine (Compound No. 3.26); 4-methyl-6-cyclopropyl-2-[1-(2,5-dimethylphenyl)-ethylidenehydrazino]-pyrimidine (Compound No. 1.35); 4-methyl-6-cyclopropyl-2-[1-(2-bromophenyl)-ethylidenehydrazino]-pyrimidine (Compound No. 1.45); 4-methyl-6-thiomethyl-2-[1-(2-methylphenyl)-ethylidenehydrazino]-pyrimidine (Compound No. 1.168).

The compounds of formula I are prepared by
1. reacting an aromatic ketone of formula II

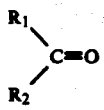

with a hydrazinopyrimidine of formula III

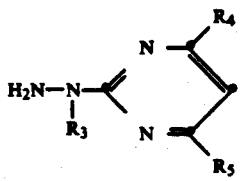

or with a salt thereof, in an inert solvent or in the molten state at temperatures of $-20°$ to $200°$ C., preferably $20°$ C. to the boiling point of the solvent used, in which reaction the solvent can also be the ketone of formula II, and the addition of a catalyst in the form of a small amount of an organic or inorganic acid or a base can considerably accelerate the reaction; or 2. reacting a hydrazone of formula IV

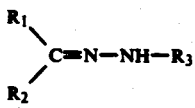

with a pyrimidine of formula V

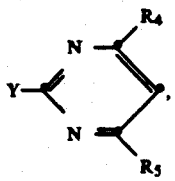

wherein Y is halogen, preferably chlorine or bromine, $C_1$-$C_4$alkoxy, preferably methoxy or ethoxy, phenoxy, mercapto, $C_1$-$C_4$alkylthio, preferably methylthio or ethylthio, phenylthio, $C_1$-$C_4$alkylsulfonyl, preferably methylsulfonyl or ethylsulfonyl, or phenylsulfonyl, in the presence of a base in an inert solvent at temperatures of $-50°$ to $150°$ C., preferably $20°$ C. to the boiling point of the solvent used; or 3. reacting an amidinohydrazone of formula VI

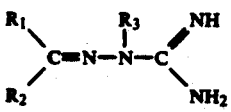

with a diketone of formula VII

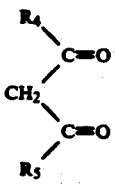

in an inert solvent or in a molten state at temperatures of $-20°$ to $200°$ C., preferably $20°$ C. to the boiling point of the solvent used, in which reaction the solvent can also be the diketone of the formula VII.

Furthermore, compounds of formula I wherein $R_3$ is $C_1$-$C_6$alkyl or CO-$R_7$ and $R_7$ is $C_1$-$C_6$alkyl, or $C_1$-$C_6$alkyl substituted at least once by halogen and/or by $C_1$-$C_3$alkoxy are prepared by reacting a compound of formula Ia

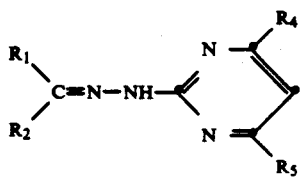

(a) with a compound of formula VIII $$R_3\text{-}Z \quad (VIII),$$

wherein Z is a customary leaving group, for example halogen or sulfonyloxy, in the presence of a strong acid or without a strong acid in an inert solvent; or (b) with a reactive derivative of an acid of formula $$R_7\text{-COOH} \quad (IX),$$

suitable reactive derivatives of compounds of formula IX being the halides, preferably chlorides or bromides, or the anhydrides.

Furthermore, compounds of formula Ic

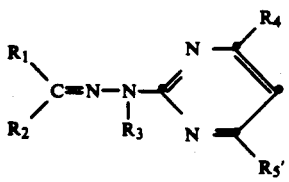

wherein $R_5'$ is chlorine or bromine, are prepared by reacting a compound of formula Ib

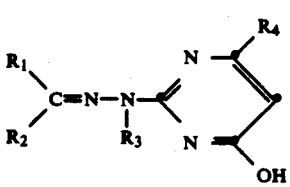

with phosphorus oxychloride or phosphorus oxybromide in an inert solvent at temperatures of $-20°$ to $180°$ C., preferably $20°$ C. to the boiling point of the solvent used, it also being possible to use the respective phosphorus oxyhalide as solvent.

Furthermore, compounds of formula Id

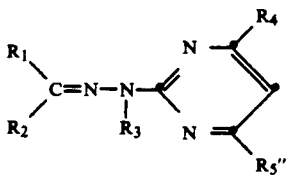 (Id)

wherein $R_5''$ is $C_1-C_3$alkoxy, $C_1-C_3$haloalkoxy or $C_1-C_3$alkylthio, are prepared by reacting a compound of formula Ic (given above) with a compound of formula XI $$R^a\text{-}X\text{-}M \qquad (XI)$$

wherein $R^a$ is $C_1-C_3$alkyl or $C_1-C_3$haloalkyl, X is oxygen or sulfur and M is hydrogen or preferably a metal atom, especially an alkali metal atom, in an inert solvent at temperatures of $-20°$ to $180°$ C., preferably $20°$ C. to the boiling point of the solvent used, and in the case where M is hydrogen, the compound XI can be used also as solvent.

In the preparation processes described above, the symbols $R_1$ to $R_5$ are as defined under formula I.

The compounds of formula III are prepared by reacting a hydrazine derivative of formula X $$R_3\text{-NH-NH}_2 \qquad (X)$$

with a pyrimidine derivative of formula V

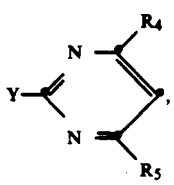 (V)

wherein Y is halogen, preferably chlorine or bromine, $C_1-C_4$alkoxy, preferably methoxy or ethoxy, phenoxy, mercapto, $C_1-C_4$alkylthio, preferably methylthio or ethylthio, phenylthio, $C_1-C_4$alkylsulfonyl, perferably methylsulfonyl or ethylsulfonyl, or phenylsulfonyl, in the presence of a base in an inert solvent at temperatures of $-50°$ to $150°$ C., preferably $20°$ C. to the boiling point of the solvent used (D.J. Brown, The Pyrimidines, Interscience Publishers, 1962; Bull. Soc. Chim. Belg. 68, 30, 1959; Chemical Pharmaceutical Bulletin 17, 1479, 1969; Australian J. Chem. 30, 2515, 1977).

The hydrazone derivatives of formula IV are known or can be prepared according to known methods, for example by reaction of a ketone derivative of formula II with a hydrazine derivative of formula X [Eur. J. Med. Chem.-Chim. Ther. 12(5), 427, 1977; Org. Syn. 50, 102, 1970; J. Pharm. Sci. 61(10), 1571, 1972].

Some of the pyrimidine derivatives of formula V are known or they can be prepared according to known methods (D.J. Brown, The Pyrimidines, Interscience Publishers, 1962).

Some of the amidinohydrazones of formula VI are known or they can be prepared according to known methods, for example by reaction of a ketone derivative of formula II with a salt of an aminoguanidine derivative of formula

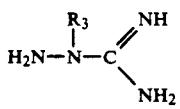

in the presence of a base (Liebigs Annalen der Chemie 307, 293, 1899).

In the processes described above, for example the following solvents may be used in conformity with the particular reaction conditions: halogenated hydrocarbons, especially chlorinated hydrocarbons, such as tetrachloroethylene, tetrachloroethane, dichloropropane, methylene chloride, dichlorobutane, chloroform, chloronaphthalene, carbon tetrachloride, trichloroethane, trichloroethylene, pentachloroethane, difluorobenzene, 1,2-dichloroethane, 1,1-dichloroethane, 1,2-cisdichloroethylene, chlorobenzene, fluorobenzene, bromobenzene, dichlorobenzene, dibromobenzene, chlorotoluene, trichlorotoluene; ethers, such as ethyl propyl ether, methyl tert.-butyl ether, n-butyl ethyl ether, di-n-butyl ether, diisobutyl ether, diisoamyl ether, diisopropyl ether, anisole, cyclohexyl methyl ether, diethyl ether, ethylene glycol dimethyl ether, ethylene glycol diethyl ether, tetrahydrofuran, dioxane, dimethoxyethane, thioanisole, dichlorodiethyl ether; nitrohydrocarbons, such as nitromethane, nitroethane, nitrobenzene, chloronitrobenzene, o-nitrotoluene; nitriles, such as acetonitrile, butyronitrile, isobutyronitrile, benzonitrile, m-chlorobenzonitrile; aliphatic or cycloaliphatic hydrocarbons, such as heptane, hexane, octane, nonane, cymol, petroleum fractions within a boiling point range of 70° C. to 190° C., cyclohexane, methylcyclohexane, decalin, petroleum ether, ligroin, trimethylpentane, such as 2,3,3-trimethylpentane; esters, such as ethyl acetate, acetoacetic acid ester, isobutyl acetate; amides, for example formamide, methylformamide, dimethylformamide; ketones, such as acetone, methyl ethyl ketone; alcohols, especially lower aliphatic alcohols, for example methanol, ethanol, n-propanol, isopropanol and the butanol isomers; and aromatic hydrocarbons, such as benzene, toluene, xylenes. Mixtures of the mentioned solvents and diluents are also suitable.

The proton acceptors used are, for example, inorganic or organic bases, for example alkali metal or alkaline earth metal compounds, for example the hydroxides, oxides or carbonates of lithium, sodium, potassium, magnesium, calcium, strontium and barium, or alternatively hydrides, for example sodium hydride. Suitable organic bases are, for example, tertiary amines, such as triethylamine, triethylenediamine and pyridine.

As acids it is possible to use both inorganic acids, for example hydrohalic acids, for example hydrofluoric acid, hydrochloric acid or hydrobromic acid, and sulfuric acid, phosphoric acid or nitric acid, and suitable organic acids, such as inter alia acetic acid, benzenesulfonic acid, toluenesulfonic acid, alkanoic acid, for example methanoic acid.

The radicals $R_1$ to $R_5$ indicated in the compounds of the afore-described processes are as defined under formula I.

The compounds of formula III are novel and the present invention relates also to them. They are defined as follows:

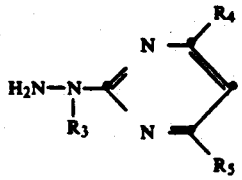

(III)

wherein: $R_3$ is hydrogen, $C_1-C_6$alkyl or $CO-R_7$; $R_4$ is $C_3-C_6$cycloalkyl, $C_3-C_6$cycloalkyl substituted up to 3 times by halogen and/or by methyl, $C_1-C_4$alkyl substituted at least once by halogen, hydroxy and/or by cyano, $C_2-C_5$alkynyl, $C_1-C_4$alkylthio or the radical $CH_2XR_8$; $R_5$ is hydrogen, $C_1-C_6$alkyl, $C_1-C_6$alkyl substituted at least once by halogen, hydroxy, cyano and/or by $C_1-C_3$alkoxy, $R_5$ is also $C_3-C_5$alkenyl, halogen, $C_1-C_3$alkoxy, $C_1-C_3$haloalkoxy, $C_3-C_6$cycloalkyl or $C_1-C_3$alkylthio; $R_8$ is $C_1-C_6$alkyl, $C_1-C_6$alkyl substituted at least once by halogen, hydroxy, cyano and/or by $C_1-C_4$alkoxy, $C_3-C_6$alkenyl, $C_3-C_6$alkynyl or $C_3-C_6$cycloalkyl; X is oxygen or sulfur.

Surprisingly, it has been found that the compounds of formula I have, for practical field application purposes, a very advantageous biocidal spectrum against phytopathogenic microorganisms, especially fungi. Compounds of formula I have very advantageous curative, preventive and, in particular, systemic properties, and can be used for protecting numerous cultivated plants. With the compounds of formula I it is possible to inhibit or destroy the pests which occur in plants or in parts of plants (fruit, blossoms, leaves, stems, tubers, roots) in different crops of useful plants, while at the same time the parts of plants which grow later are also protected, for example, from attack by phytopathogenic microorganisms.

The compounds of formula I are effective, for example, against the phytopathogenic fungi belonging to the following classes: Fungi imperfecti (especially Botrytis, also Pyricularia, Helminthosporium, Fusarium, Septoria, Cercospora and Alternaria); Basidiomycetes (for example Rhizoctonia, Hemileia, Puccinia). They are also effective against the class of Ascomycetes (for example Venturia and Erysiphe, Podosphaera, Monilinia, Uncinula) and the class of Oomycetes (for example Phytophthora, Pythium, Plasmopara). The compounds of formula I can also be used as dressing agents for protecting seeds (fruit, tubers, grains) and plant cuttings against fungus infections as well as against phytopathogenic fungi which occur in the soil.

The invention also relates to compositions containing as active ingredient compounds of formula I, especially plant-protecting compositions, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise, for example, the following species of plants: cereals (wheat, barley, rye, oats, rice, maize, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, sugar cane, tea, pepper, vines, hops, bananas and natural rubber plants, as well as ornamentals.

The compounds of formula I are normally applied in the form of compositions and can be applied to the crop area or plant to be treated, simultaneously or in succession, with further compounds. These compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen. However, the compounds of formula I can also penetrate the plant through the roots via the soil (systemic action) if the locus of the plant is impregnated with a liquid formulation, or if the compounds are applied in solid form to the soil, e.g. in granular form (soil application). In paddy rice crops, such granulates may be applied in metered amounts to the flooded rice field. The compounds of formula I may, however, also be applied to seeds (coating) by impregnating the seeds either with a liquid formulation containing a compound of formula I, or coating them with a solid formulation.

The compounds of formula I are used in unmodified form or, preferably, together with the adjuvants conventionally employed in the art of formulation and are therefore advantageously formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, especially from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

The agrochemical compositions usually contain 0.1 to 99% by weight, preferably 0.1 to 95% by weight, of a compound of formula I, 99.9 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normal employ dilute formulations.

The compositions may also contain further auxiliaries, such as stabilisers, antifoams, viscosity regulators, binders, tackifiers as well as fertilisers or other active ingredients for obtaining special effects.

The following Examples serve to illustrate the invention in more detail but do not constitute a limitation thereof.

1. PREPARATION EXAMPLES

EXAMPLE 1.1

Preparation of 4-methyl-6-cyclopropyl-2-[1-(2-methylphenyl)-ethylidenehydrazino]-pyrimidine

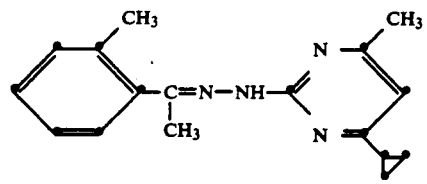

3.3 g of 2-hydrazino-4-methyl-6-cyclopropylpyrimidine and 2.7 g of 2-methylacetophenone are heated to boiling in 40 ml of ethanol and boiled under reflux for 20 hours with stirring. The reaction solution is then cooled and the solvent is evaporated off in vacuo. For purification, the oily residue is chromatographed using hexane/ethyl acetate (2:1) over a column of silica gel.

First the E-form, then the E/Z mixture and finally the Z-form of the title compound is eluted.

The various fractions are isolated separately.

E-form:
Melting point: 121°–122° C.
Z-form:
Melting point: 96°–98° C.
E/Z mixture:
Melting point: 92°–93° C.
Classification is made by means of NMR spectra.

EXAMPLE 1.2

Preparation of 2-hydrazino-4-methyl-6-cyclopropylpyrimidine

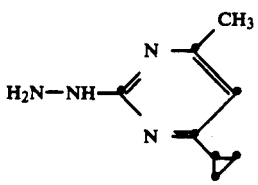

3.0 g of 2-chloro-4-methyl-6-cyclopropylpyrimidine are dissolved in 30 ml of ethanol; 3.8 ml of hydrazine hydrate are added and the mixture is stirred for 20 hours at room temperature. The solvent is then evaporated off in vacuo and the residue is recrystallised with ethyl acetate. M.p. 98°–99° C.

TABLE 1

Compounds of formula

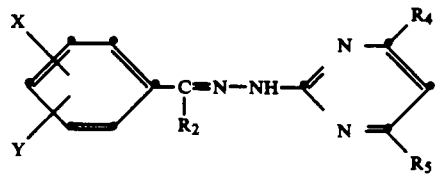

| Comp. No. | X | Y | R₂ | R₄ | R₅ | physical constant |
|---|---|---|---|---|---|---|
| 1.1 | 2-CH₃ | H | CH₃ |  | CH₃ | m.p. 92–93° C. |

TABLE 1-continued

Compounds of formula

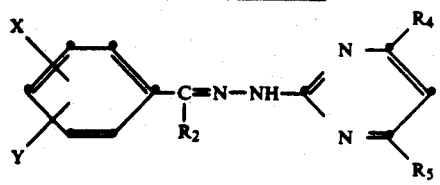

| Comp. No. | X | Y | $R_2$ | $R_4$ | $R_5$ | physical constant |
|---|---|---|---|---|---|---|
| 1.2 | 2-$CH_3$ | 4-$CH_3$ | $CH_3$ | cyclopropyl | $CH_3$ | m.p. 133–134° C. |
| 1.3 | 3-Cl | H | $CH_3$ | cyclopropyl | $CH_3$ | m.p. 124–125° C. |
| 1.4 | 2-$CH_3$ | H | $CH_3$ | $CH_2F$ | $CH_3$ | |
| 1.5 | 2-$CH_3$ | H | $CH_3$ | $CF_3$ | $CH_3$ | m.p. 125–135° C. |
| 1.6 | 2-$CH_3$ | H | phenyl | $CH_2OCH_3$ | $CH_3$ | |
| 1.7 | 2-Cl | H | $CH_3$ | C≡CH | $CH_3$ | |
| 1.8 | 4-Cl | H | cyclopropyl | cyclopropyl | $CH_3$ | m.p. 100–102° C. |
| 1.9 | 2-F | H | $CH_3$ | cyclopropyl | $CH_3$ | m.p. 115–118° C. |
| 1.10 | H | H | phenyl | cyclopropyl | $CH_3$ | m.p. 99–101° C. |
| 1.11 | 2-$CH_3$ | H | $CH_3$ | $CH_2OCH_3$ | $CH_3$ | $n_D^{29}$: 1.5953 |
| 1.12 | 2-CN | H | $CH_3$ | $CF_3$ | $CH_3$ | |
| 1.13 | 2-Cl | H | $CH_3$ | cyclopropyl | $CH_3$ | m.p. 139–140° C. |
| 1.14 | 2-$OCHF_2$ | 4-Cl | $CH_3$ | cyclopropyl | $CH_3$ | |
| 1.15 | 2-Cl | 4-Cl | $CH_3$ | cyclopropyl | $CH_3$ | |
| 1.16 | 2-$CH_3$ | 4-$CH_3$ | $CH_3$ | $CF_3$ | $CH_3$ | |

TABLE 1-continued
Compounds of formula
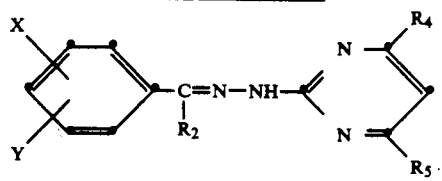
| Comp. No. | X | Y | R₂ | R₄ | R₅ | physical constant |
|---|---|---|---|---|---|---|
| 1.17 | 4-CH₃ | H | CH₃ | △ | CH₃ | m.p. 176–177° C. |
| 1.18 | 2-Cl | H | phenyl | △ | CH₃ | m.p. 89–92° C. |
| 1.19 | 2-CH₃ | 5-CH₃ | CH₃ | CH₂OCH₃ | CH₃ | |
| 1.20 | 2-SCH₃ | H | CH₃ | △ | CH₃ | |
| 1.21 | 2-CH₃ | 4-CH₃ | CH₃ | CH₂F | CH₃ | |
| 1.22 | 2-CH₃ | H | CH₃ | △ | CH₂OCH₃ | |
| 1.23 | 4-Cl | H | CH₃ | △ | CH₃ | m.p. 168–169° C. |
| 1.24 | 2-CH₃ | H | CH₃ | △ | △ | |
| 1.25 | 3-F | H | CH₃ | △ | CH₃ | |
| 1.26 | 2-CH₃ | 4-CH₃ | CH₃ | CH₂OCH₃ | CH₃ | |
| 1.27 | 2-CH₃ | H | CH₃ | △ | OCH₃ | |
| 1.28 | 2-Br | H | CH₃ | CF₃ | CH₃ | |
| 1.29 | 2-OCH₃ | H | CH₃ | △ | CH₃ | m.p. 83–85° C. |
| 1.30 | 2-CH₃ | 4-OCHF₂ | CH₃ | △ | CH₃ | $n_D^{52}$: 1.5672 |

TABLE 1-continued

Compounds of formula

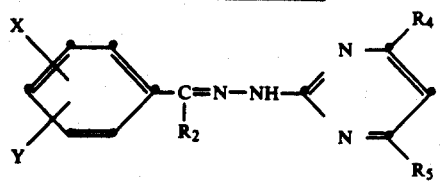

| Comp. No. | X | Y | $R_2$ | $R_4$ | $R_5$ | physical constant |
|---|---|---|---|---|---|---|
| 1.31 | 2-$CH_3$ | H | $CH_3$ | $CH_2OCH_3$ | Cl | m.p. 116–117° C. |
| 1.32 | H | H | $(CH_2)_3CH_3$ | △ | $CH_3$ | |
| 1.33 | 2-$CH_3$ | H | phenyl | △ | $CH_3$ | $n_D^{52}$: 1.6258 |
| 1.34 | 2-Cl | H | $CH_3$ | $CF_3$ | $CH_3$ | |
| 1.35 | 2-$CH_3$ | 5-$CH_3$ | $CH_3$ | △ | $CH_3$ | m.p. 119–121° C. |
| 1.36 | 2-$CH_3$ | H | $CH_2CH_3$ | △ | $CH_3$ | |
| 1.37 | 2-$CH_3$ | H | $CH_3$ | C≡C—$CH_3$ | $CH_3$ | |
| 1.38 | H | H | $CH_3$ | △ | $CH_3$ | m.p. 108–112° C. |
| 1.39 | 3-$CH_3$ | H | $CH_3$ | △ | $CH_3$ | m.p. 121.5–122° C. |
| 1.40 | 2-$CH_3$ | H | $CH_3$ | △ | Cl | |
| 1.41 | 2-$CF_3$ | H | $CH_3$ | △ | $CH_3$ | m.p. 147–151° C. |
| 1.42 | 2-Cl | H | $CH_3$ | C≡C—$CH_3$ | $CH_3$ | |
| 1.43 | 2-$CH_3$ | H | $CH_3$ | cyclobutyl | $CH_3$ | |
| 1.44 | 2-$CH_3$ | H | $CH_3$ | $CH_2OCH_2CH_3$ | $CH_3$ | |

TABLE 1-continued

Compounds of formula

| Comp. No. | X | Y | R$_2$ | R$_4$ | R$_5$ | physical constant |
|---|---|---|---|---|---|---|
| 1.45 | 2-Br | H | CH$_3$ | cyclopropyl | CH$_3$ | m.p. 128–134° C. |
| 1.46 | 2-NO$_2$ | H | CH$_3$ | cyclopropyl | CH$_3$ | m.p. 106–110° C. |
| 1.47 | 2-CH$_3$ | 4-OCHF$_2$ | CH$_3$ | CH$_2$OCH$_3$ | CH$_3$ | |
| 1.48 | 2-CH$_3$ | 4-CH$_3$ | CH$_3$ | C≡C—CH$_3$ | CH$_3$ | |
| 1.49 | 2-CH$_3$ | H | CH$_3$ | cyclopropyl | OCHF$_2$ | |
| 1.50 | 2-OCHF$_2$ | H | CH$_3$ | cyclopropyl | CH$_3$ | m.p. 120–122° C. |
| 1.51 | 2-CH$_3$ | H | CH$_3$ | CH$_2$Cl | CH$_3$ | |
| 1.52 | 3-CH$_3$ | 4-CH$_3$ | CH$_3$ | cyclopropyl | CH$_3$ | m.p. 154–155° C. |
| 1.53 | 2-CH$_3$ | H | CH$_3$ | cyclopropyl | CH$_2$F | |
| 1.54 | 2-CH$_3$ | 5-CH$_3$ | CH$_3$ | CH$_2$F | CH$_3$ | |
| 1.55 | 2-Cl | 5-Cl | CH$_3$ | cyclopropyl | CH$_3$ | |
| 1.56 | 2-CH$_3$ | 4-CH$_3$ | phenyl | cyclopropyl | CH$_3$ | |
| 1.57 | 2-CH$_3$ | 4-OCHF$_2$ | CH$_3$ | C≡C—CH$_3$ | CH$_3$ | |
| 1.58 | 2-Cl | H | 4-F-phenyl | cyclopropyl | CH$_3$ | |

TABLE 1-continued

Compounds of formula

| Comp. No. | X | Y | R₂ | R₄ | R₅ | physical constant |
|---|---|---|---|---|---|---|
| 1.59 | 2-CH₃ | H | (benzyl) | CH₂F | CH₃ | |
| 1.60 | 2-CH₃ | H | CH₃ | (cyclopropyl) | CF₃ | |
| 1.61 | 2-CH₃ | 4-CH₃ | (benzyl) | CH₂OCH₃ | CH₃ | |
| 1.62 | 2-CH₃ | 4-Cl | CH₃ | (cyclopropyl) | CH₃ | |
| 1.63 | H | H | CH₂-(phenyl) | (cyclopropyl) | CH₃ | $n_D^{54}$: 1.6290 |
| 1.64 | 2-CH₃ | H | CH₃ | C≡CCH₂CH₂CH₃ | CH₃ | |
| 1.65 | 2-Cl | H | CH₃ | (cyclopropyl) | OCH₃ | |
| 1.66 | 2-CH₃ | H | CH₃ | CH₂OCH₃ | OCH₃ | $n_D^{49}$: 1.5800 |
| 1.67 | 2-CH₃ | H | CH₃ | C≡C—CH₃ | Cl | |
| 1.68 | 2-CH₃ | H | CH₃ | (cyclopropyl)-CH₃ | CH₂F | |
| 1.69 | 2-CH₃ | H | CH₃ | (cyclohexyl) | CH₃ | |
| 1.70 | 2-Cl | H | CH₃ | CH₂OCH₃ | CH₂CH₃ | |
| 1.71 | 2-CH₃ | H | CH₃ | (cyclopropyl) | CH₂OH | |
| 1.72 | 2-CH₃ | H | CH₃ | (cyclopropyl)-CH₃ | CH₃ | |

TABLE 1-continued

Compounds of formula

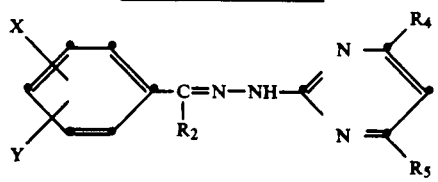

| Comp. No. | X | Y | $R_2$ | $R_4$ | $R_5$ | physical constant |
|---|---|---|---|---|---|---|
| 1.73 | 2-Cl | H | $CH_3$ | $CH_2OCH_3$ | $CH_3$ | |
| 1.74 | 2-$CH_3$ | H | $CH_3$ | C≡CH | $CH_3$ | |
| 1.75 | 2-$CH_3$ | 3-$CH_3$ | $CH_3$ | cyclopropyl | $CH_3$ | |
| 1.76 | 2-$OCH_3$ | H | $CH_3$ | $CH_2OCH_3$ | $CH_3$ | |
| 1.77 | 2-$CH_3$ | 4-$OCH_3$ | $CH_3$ | cyclopropyl | $CH_3$ | m.p. 108–113° C. |
| 1.78 | 2-Cl | H | $CH_3$ | cyclopropyl | $CH_2F$ | |
| 1.79 | 2-Br | H | $CH_3$ | C≡C—$CH_3$ | $CH_3$ | |
| 1.80 | H | H | $CH_2$-phenyl | $CH_2OCH_3$ | $CH_3$ | |
| 1.81 | 2-$CH_3$ | 4-$CH_3$ | phenyl | cyclopropyl | $CH_2F$ | |
| 1.82 | 2-Cl | 4-Cl | $CH_3$ | $CH_2OCH_3$ | $CH_3$ | |
| 1.83 | 2-$CH_3$ | H | $CH_3$ | cyclopropyl | $CH_2CH_3$ | |
| 1.84 | 2-$CH_3$ | H | $CH_3$ | $CHCl_2$ | $CH_3$ | |
| 1.85 | 2-$CH_3$ | H | $CH_3$ | $CF_2CF_3$ | $CH_3$ | |
| 1.86 | 2-$CH_3$ | H | $CH_3$ | $CH_2OCH_3$ | $CF_3$ | |
| 1.87 | 2-Cl | H | $CH_3$ | $CHCl_2$ | $CH_3$ | |
| 1.88 | 2-$CH_3$ | H | $CH_3$ | $CF_2Cl$ | $CH_3$ | |
| 1.89 | 2-$CH_3$ | H | $CH_3$ | $CH_2OCH_3$ | $CF_2Cl$ | |
| 1.90 | 2-$CH_3$ | H | $CH_3$ | $CH(CH_3)_2$ | $CF_3$ | |
| 1.91 | 2-Cl | H | $CH_3$ | $CF_2Cl$ | $CH_3$ | |
| 1.92 | 2-$CH_3$ | H | $CH_3$ | $(CH_2)_3CH_3$ | $CF_3$ | |
| 1.93 | 2-$CH_3$ | H | $CH_3$ | 1-methylcyclopropyl | cyclopropyl | |
| 1.94 | 2-$CH_3$ | H | $CH_3$ | C≡C—$CH_3$ | cyclopropyl | |

TABLE 1-continued

Compounds of formula $$X-C_6H_3(Y)-C(R_2)=N-NH-C(=N-)N=C(R_4)-CH=C(R_5)$$

| Comp. No. | X | Y | $R_2$ | $R_4$ | $R_5$ | physical constant |
|---|---|---|---|---|---|---|
| 1.95 | 2-$CH_3$ | 4-$CH_3$ | $CH_3$ | cyclopropyl | $CH_2CH_3$ | |
| 1.96 | 2-Br | H | $CH_3$ | $CH_2OCH_3$ | $CH_3$ | |
| 1.97 | 2-F | H | $CH_3$ | $CH_2F$ | cyclopropyl | |
| 1.98 | 2-$CH_3$ | H | $CH_3$ | $CH_2F$ | $CH_2F$ | |
| 1.99 | 2-$CH_3$ | 4-$OCH_3$ | $CH_3$ | $CH_2F$ | cyclopropyl | |
| 1.100 | 2-$CH_3$ | 4-$OCH_3$ | $CH_3$ | $C\equiv C-CH_3$ | $CH_3$ | |
| 1.101 | 2-$CH_3$ | 5-$CH_3$ | $CH_3$ | $C\equiv C-CH_3$ | $CH_3$ | |
| 1.102 | 2-$CH_3$ | H | $CF_3$ | cyclopropyl | $CH_3$ | |
| 1.103 | H | H | $CO_2CH_2CH_3$ | cyclopropyl | $CH_3$ | |
| 1.104 | 2-$CH_3$ | 5-$CH_3$ | $CH_3$ | $CH_2F$ | cyclopropyl | |
| 1.105 | 2-$CH_3$ | H | $CH_2$-cyclopropyl | cyclopropyl | $CH_3$ | |
| 1.106 | 2-$CH_3$ | H | $CH_2OCH_3$ | cyclopropyl | $CH_3$ | |
| 1.107 | 2-$CH_3$ | H | 2-methylphenyl | cyclopropyl | $CH_3$ | |
| 1.108 | 2-$CH_3$ | H | $CH_2$-phenyl | cyclopropyl | $CH_3$ | |

TABLE 1-continued

Compounds of formula $$X-C_6H_3(Y)-C(R_2)=N-NH-C(=N-)(N=)\text{ pyrimidine with }R_4, R_5$$

| Comp. No. | X | Y | R$_2$ | R$_4$ | R$_5$ | physical constant |
|---|---|---|---|---|---|---|
| 1.109 | 2-CH$_3$ | H | CH$_2$-phenyl | CH$_2$OCH$_3$ | CH$_3$ | |
| 1.110 | 2-CH$_3$ | H | CH$_2$-(4-Cl-phenyl) | cyclopropyl | CH$_3$ | |
| 1.111 | 2-CH$_3$ | H | CH$_3$ | CH$_2$CN | cyclopropyl | |
| 1.112 | 2-Cl | H | CH$_3$ | CH$_2$OH | cyclopropyl | |
| 1.113 | 2-CH$_3$ | H | CH$_3$ | CH$_2$Br | cyclopropyl | |
| 1.114 | 2-CH$_3$ | H | CH$_3$ | CF$_3$ | CH(OCH$_3$)$_2$ | |
| 1.115 | 2-CH$_3$ | H | CH$_3$ | CH$_2$OH | cyclopropyl | |
| 1.116 | 2-CH$_3$ | H | CH$_2$CH$_3$ | C≡C—CH$_3$ | CH$_3$ | |
| 1.117 | 2-CH$_3$ | 4-CH$_3$ | CH$_2$CH$_3$ | CH$_2$OCH$_3$ | CH$_3$ | |
| 1.118 | 2-F | H | CH$_3$ | C≡C—CH$_3$ | CH$_3$ | |
| 1.119 | 2-CH$_3$ | H | phenyl | cyclopropyl | CH$_2$F | |
| 1.120 | 2-Cl | H | phenyl | CH$_2$OCH$_3$ | CH$_3$ | |
| 1.121 | 2-CH$_3$ | H | phenyl | C≡C—CH$_3$ | CH$_3$ | |
| 1.122 | 2-Cl | H | phenyl | cyclopropyl | CH$_2$F | |

TABLE 1-continued

Compounds of formula

[structure: X,Y-substituted phenyl-C(R2)=N-NH-C(=N-)(N=) with R4, R5 on pyrimidine ring]

| Comp. No. | X | Y | R₂ | R₄ | R₅ | physical constant |
|---|---|---|---|---|---|---|
| 1.123 | 2-Cl | H | phenyl | CH₂F | CH₃ | |
| 1.124 | 2-Cl | H | phenyl | C≡C—CH₃ | CH₃ | |
| 1.125 | 2-CH₂CH₃ | H | CH₃ | cyclopropyl | CH₃ | $n_D^{49}$: 1.5959 |
| 1.126 | 2-CH₂CH₃ | 4-CH₂CH₃ | CH₃ | CH₂OCH₃ | CH₃ | |
| 1.127 | 2-CH₂CH₃ | H | CH₃ | CH₂F | cyclopropyl | |
| 1.128 | 2-CH₂CH₃ | H | CH₃ | C≡C—CH₃ | CH₃ | |
| 1.129 | 2-CH₂CH₃ | H | CH₃ | CH₂OCH₃ | CH₃ | |
| 1.130 | 3-CH₃ | 4-CH₃ | CH₃ | CH₂F | cyclopropyl | |
| 1.131 | 2-CH(CH₃)₂ | H | CH₃ | cyclopropyl | CH₃ | |
| 1.132 | 2-CH₃ | 4-C(CH₃)₃ | CH₃ | cyclopropyl | CH₃ | |
| 1.133 | 2-CH₃ | 4-SCH₃ | CH₃ | cyclopropyl | CH₃ | |
| 1.134 | 2-CH(CH₃)₂ | H | CH₃ | CH₂OCH₃ | CH₃ | |
| 1.135 | 2-CH₃ | 4-SOCH₃ | CH₃ | cyclopropyl | CH₃ | |
| 1.136 | 2-CH(CH₃)₂ | H | CH₃ | CH₂F | cyclopropyl | |

TABLE 1-continued

Compounds of formula $$X-C_6H_3(Y)-C(R_2)=N-NH-\text{pyrimidine}(R_4, R_5)$$

| Comp. No. | X | Y | $R_2$ | $R_4$ | $R_5$ | physical constant |
|---|---|---|---|---|---|---|
| 1.137 | 2-$CH_3$ | 4-$SO_2CH_3$ | $CH_3$ | cyclopropyl | $CH_3$ | |
| 1.138 | 2-Cl | 5-$CH_3$ | $CH_3$ | cyclopropyl | $CH_3$ | |
| 1.139 | 2-$CH_3$ | H | $CH_3$ | cyclopropyl | H | |
| 1.140 | 2-Cl | H | $CH_3$ | $CH_2OCH_3$ | $SCH_3$ | |
| 1.141 | 2-Cl | 5-$CH_3$ | $CH_3$ | $CH_2F$ | cyclopropyl | |
| 1.142 | 2-$CH_3$ | 4-Cl | $CH_3$ | $C{\equiv}C-CH_3$ | $CH_3$ | |
| 1.143 | 2-Cl | 4-Cl | $CO_2C_2H_5$ | cyclopropyl | $CH_3$ | |
| 1.144 | 2-$CH_3$ | 4-Cl | $CH_3$ | $CH_2OCH_3$ | $CH_3$ | |
| 1.145 | 2-$CH_3$ | 4-Cl | $CH_3$ | $CH_2F$ | cyclopropyl | |
| 1.146 | 2-$CH_3$ | 4-Cl | $CH_3$ | $CH_2F$ | $CH_3$ | |
| 1.147 | 2-Cl | 6-Cl | $CH_3$ | cyclopropyl | $CH_3$ | |
| 1.148 | 2-OH | H | $CH_3$ | cyclopropyl | $CH_3$ | m.p. 132–136° C. |
| 1.149 | H | H | cyclopropyl | cyclopropyl | $CH_3$ | $n_D^{24.5}$: 1.6262 |
| 1.150 | 2-$CH_3$ | 4-OH | $CH_3$ | cyclopropyl | $CH_3$ | m.p. 160–163° C. |

TABLE 1-continued

Compounds of formula

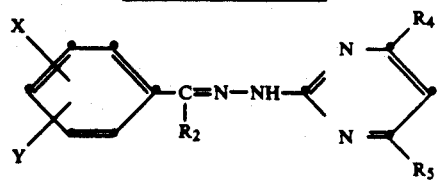

| Comp. No. | X | Y | R2 | R4 | R5 | physical constant |
|---|---|---|---|---|---|---|
| 1.151 | 2-CH3 | H | CH3 | (cyclopropyl) | Allyl | |
| 1.152 | 2-CH3 | H | CH3 | CH2OCH3 | Allyl | |
| 1.153 | 2-CH3 | H | CH3 | CH2F | Allyl | |
| 1.154 | 2-CH3 | H | CH3 | CH2OCH3 | OH | m.p. 80–82° C. |
| 1.155 | 2-F | H | CH3 | CF3 | CH3 | m.p. 147–148° C. |
| 1.156 | 2-CH3 | 5-CH3 | CH3 | CF3 | CH3 | m.p. 99–100° C. |
| 1.157 | 2-CH3 | 5-CH3 | CH3 | CH2OCH3 | OCH3 | $n_D^{36}$: 1.5809 |
| 1.158 | 2-NO2 | H | CH3 | CF3 | CH3 | m.p. 155–160° C. |
| 1.159 | 2-CF3 | H | CH3 | CF3 | CH3 | m.p. 129–130° C. |
| 1.160 | 2-Cl | H | CH3 | CH2OCH3 | OH | m.p. 88–92° C. |
| 1.161 | 2-Cl | H | CH3 | CH2OCH3 | Cl | m.p. 122–123° C. |
| 1.162 | 2-OCHF2 | H | CH3 | CH2OCH3 | OH | m.p. 94–95° C. |
| 1.163 | 2-OCHF2 | H | CH3 | CH2OCH3 | Cl | m.p. 85–88° C. |
| 1.164 | 2-OCHF2 | H | CH3 | CF3 | CH3 | m.p. 115–116° C. |
| 1.165 | 2-Cl | H | CH3 | CH2OCH3 | OCH3 | m.p. 102–103° C. |
| 1.166 | 2-CH3 | 5-CH3 | CH3 | CH2OCH3 | SCH3 | m.p. 127–128° C. |
| 1.167 | 2-CH3 | 4-F | CH3 | (cyclopropyl) | CH3 | m.p. 161–162° C. |
| 1.168 | 2-CH3 | H | CH3 | SCH3 | CH3 | |
| 1.169 | 2-Br | H | CH3 | SCH3 | CH3 | |
| 1.170 | 2-F | H | CH3 | SCH3 | CH3 | |
| 1.171 | 2-CH3 | H | CH3 | S—C2H5 | CH3 | |
| 1.172 | 2-CH3 | 5-CH3 | CH3 | S—CH3 | CH3 | |
| 1.173 | 2-CH3 | H | CH3 | (cyclopropyl) | SCH3 | |

TABLE 2

Compounds of formula

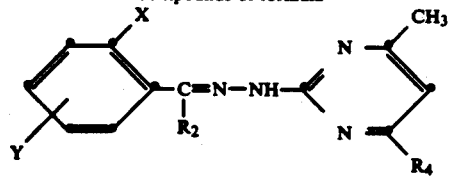

| Comp. No. | X | Y | R2 | R4 | isomeric form | physical constant |
|---|---|---|---|---|---|---|
| 2.1 | CH3 | H | CH3 | (cyclopropyl) | Z | m.p. 96–98° C. |
| 2.2 | CH3 | H | CH3 | (cyclopropyl) | E | m.p. 121–122° C. |
| 2.3 | CH3 | H | CH3 | CH2F | E | |
| 2.4 | CH3 | H | CH3 | CH2F | Z | |

TABLE 2-continued

Compounds of formula

| Comp. No. | X | Y | R₂ | R₄ | isomeric form | physical constant |
|---|---|---|---|---|---|---|
| 2.5 | CH₃ | H | CH₃ | CF₃ | Z | m.p. 136–137° C. |
| 2.6 | CH₃ | H | CH₃ | CF₃ | E | m.p. 150–151° C. |
| 2.7 | CH₃ | H | CH₃ | CH₂OCH₃ | E | $n_D^{27}$: 1.6015 |
| 2.8 | CH₃ | H | CH₃ | CH₂OCH₃ | Z | $n_D^{27}$: 1.5712 |
| 2.9 | OCHF₂ | H | CH₃ | cyclopropyl | Z | m.p. 147–150° C. |
| 2.10 | OCHF₂ | H | CH₃ | cyclopropyl | E | m.p. 93–96° C. |
| 2.11 | CH₃ | H | CH₃ | C≡C—CH₃ | E | |
| 2.12 | CH₃ | H | CH₃ | C≡C—CH₃ | Z | |
| 2.13 | CH₃ | H | CH₃ | methylcyclopropyl | E | |
| 2.14 | CH₃ | H | CH₃ | methylcyclopropyl | Z | |
| 2.15 | Cl | H | CH₃ | CF₃ | E | m.p. 175–177° C. |
| 2.16 | Cl | H | CH₃ | CF₃ | Z | $n_D^{25}$: 1.5618 |
| 2.17 | NO₂ | H | CH₃ | cyclopropyl | E | m.p. 144–146° C. |
| 2.18 | NO₂ | H | CH₃ | cyclopropyl | Z | m.p. 144–146° C. |
| 2.19 | H | H | CH₂—phenyl | cyclopropyl | E | m.p. 91–92° C. |
| 2.20 | CH₂CH₃ | H | CH₃ | cyclopropyl | E | m.p. 83–85° C. |
| 2.21 | CH₃ | 4-OCHF₂ | CH₃ | cyclopropyl | E | m.p. 115–116° C. |
| 2.22 | Br | H | CH₃ | CF₃ | E | m.p. 172–173° C. |
| 2.23 | NO₂ | H | CH₃ | CF₃ | E | m.p. 191–192° C. |
| 2.24 | 2-CH₃ | 4-CH₃ | CH₃ | CF₃ | E | m.p. 141–142° C. |
| 2.25 | 2-CH₃ | 4-CH₃ | CH₃ | CF₃ | Z | m.p. 104–105° C. |

TABLE 2-continued

Compounds of formula

| Comp. No. | X | Y | R₂ | R₄ | isomeric form | physical constant |
|---|---|---|---|---|---|---|
| 2.26 | 2-CH₃ | 4-CH₃ | CH₃ | cyclopropyl | Z | m.p. 123–125° C. |

TABLE 3

Compounds of formula $Ar-C(R_2)=N-NH-$ [pyrimidine with $R_4$, $R_5$]

| Comp. No. | Ar | R₂ | R₄ | R₅ | physical constant |
|---|---|---|---|---|---|
| 3.1 | 2,4,5-(CH₃)₃-phenyl | CH₃ | cyclopropyl | CH₃ | |
| 3.2 | 2,3,4-Cl₃-phenyl | CH₃ | CH₂OCH₃ | CH₃ | |
| 3.3 | 2,3,4,5-(CH₃)₄-phenyl | CH₃ | cyclopropyl | CH₃ | |
| 3.4 | α-naphthyl | CH₃ | C≡C—CH₃ | CH₃ | |
| 3.5 | 2,5-(CH₃)₂-4-Cl-phenyl | CH₃ | cyclopropyl | CH₃ | |
| 3.6 | 2,4-(CH₃)₂-α-naphthyl | CH₃ | CH₂F | cyclopropyl | |
| 3.7 | β-naphthyl | CH₃ | cyclopropyl | CH₃ | m.p. 133–138° C. |
| 3.8 | 2-CH₃-4,5-Cl₂-phenyl | CH₃ | CH₂F | cyclopropyl | |
| 3.9 | 2,4-Cl₂-5-CH₃-phenyl | CH₃ | cyclopropyl | CH₃ | |
| 3.10 | 1,4-(CH₃)₂-β-naphthyl | CH₃ | CH₂OCH₃ | CH₃ | |

TABLE 3-continued

Compounds of formula

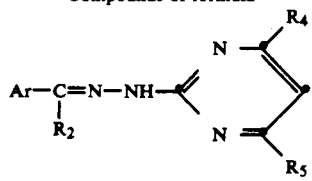

| Comp. No. | Ar | $R_2$ | $R_4$ | $R_5$ | physical constant |
|---|---|---|---|---|---|
| 3.11 | 2,3,4,5-$(CH_3)_4$-phenyl | $CH_3$ | $CH_2F$ | $CH_3$ | |
| 3.12 | α-naphthyl | $CH_3$ | △ | $CH_3$ | m.p. 123–125° C. |
| 3.13 | 2,4-$(CH_3)_2$-α-naphthyl | $CH_3$ | △ | $CH_3$ | |
| 3.14 | 2,4,5-$(CH_3)_3$-phenyl | $CH_3$ | C≡C—$CH_3$ | $CH_3$ | |
| 3.15 | α-napthyl | $CH_3$ | $CF_3$ | $CH_3$ | |
| 3.16 | 2,4,5-$(CH_3)_3$-phenyl | $CH_3$ | $CH_2OCH_3$ | $CH_3$ | |
| 3.17 | β-naphthyl | $CH_3$ | $CH_2F$ | △ | |
| 3.18 | 2-$CH_3$-4,5-$Cl_2$-phenyl | $CH_3$ | △ | $CH_3$ | |
| 3.19 | 2,4,5-$(CH_3)_3$-phenyl | $CH_3$ | $CH_2F$ | △ | |
| 3.20 | β-naphthyl | $CH_3$ | $CH_2F$ | $CH_3$ | |
| 3.21 | 2,4-$Cl_2$-5-$CH_3$-phenyl | $CH_3$ | $CH_2OCH_3$ | $CH_3$ | |
| 3.22 | 2,3,4,5-$(CH_3)_4$-phenyl | $CH_3$ | C≡C—$CH_3$ | $CH_3$ | |
| 3.23 | α-naphthyl | $CH_3$ | $CH_2OCH_3$ | $CH_3$ | |
| 3.24 | 2,3,4-$Cl_3$-phenyl | $CH_3$ | △ | $CH_3$ | |
| 3.25 | 2-$CH_3$-α-naphthyl | $CH_3$ | △ | $CH_3$ | |
| 3.26 | 2,4-$(CH_3)_2$-α-naphthyl | $CH_3$ | △ | $CH_3$ | |
| 3.27 | 2-$CH_3$-α-naphthyl | $CH_3$ | $CH_2OCH_3$ | $CH_3$ | |
| 3.28 | 2,4-$(CH_3)_2$-α-naphthyl | $CH_3$ | $CH_2OCH_3$ | $CH_3$ | |
| 3.29 | 2,3-$(CH_3)_2$-α-naphthyl | $CH_3$ | △ | $CH_3$ | |
| 3.30 | 2,3-$(CH_3)_2$-α-naphthyl | $CH_3$ | $CH_2OCH_3$ | $CH_3$ | |

TABLE 3-continued

Compounds of formula

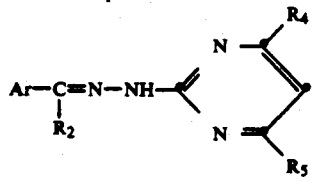

| Comp. No. | Ar | R$_2$ | R$_4$ | R$_5$ | physical constant |
|---|---|---|---|---|---|
| 3.31 | 2,4,6-(CH$_3$)$_3$-phenyl | CH$_3$ | ▷• | CH$_3$ | m.p. 139–140° C. |

TABLE 4

Compounds of formula

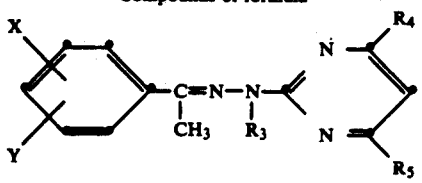

| Comp. No. | X | Y | R$_3$ | R$_4$ | R$_5$ | physical constant |
|---|---|---|---|---|---|---|
| 4.1 | 2-CH$_3$ | H | CH$_3$ | ▷• | CH$_3$ | |
| 4.2 | 2-CH$_3$ | H | COCH$_3$ | CH$_2$OCH$_3$ | CH$_3$ | |
| 4.3 | 2-Cl | H | COCHCl$_2$ | ▷• | CH$_3$ | |
| 4.4 | 2-CH$_3$ | H | CH$_3$ | ▷• | CH$_2$F | |
| 4.5 | 2-CH$_3$ | 4-CH$_3$ | CH$_2$CH$_3$ | ▷• | CH$_3$ | |
| 4.6 | 2-CH$_3$ | H | CH$_3$ | C≡C—CH$_3$ | CH$_3$ | |
| 4.7 | 2-Cl | H | COCH$_2$OCH$_3$ | ▷• | CH$_3$ | |
| 4.8 | 2-CH$_3$ | H | COCH$_2$OCH$_3$ | ▷• | CH$_3$ | |
| 4.9 | 2-F | H | CH$_3$ | ▷• | CH$_3$ | |
| 4.10 | 2-CH$_3$ | H | n-C$_3$H$_7$ | CH$_2$OCH$_3$ | CH$_3$ | |

TABLE 4-continued

Compounds of formula

[structure: X,Y-substituted phenyl-C(CH₃)=N-N(R₃)-C(=N-)(pyrimidine with R₄, R₅)]

| Comp. No. | X | Y | R₃ | R₄ | R₅ | physical constant |
|---|---|---|---|---|---|---|
| 4.11 | 2-CH₃ | H | COCCl₂CH₃ | cyclopropyl | CH₃ | |
| 4.12 | 2-CH₃ | 4-CH₃ | CH₃ | cyclopropyl | CH₃ | |
| 4.13 | 2-CH₃ | 4-OCH₃ | CH₃ | CH₂OCH₃ | CH₃ | |
| 4.14 | 2-CH₃ | 4-Cl | CH₃ | C≡C—CH₃ | CH₃ | |
| 4.15 | 2-CH₃ | H | CH₂CH₃ | CH₂OCH₃ | OCH₃ | |

TABLE 5

Compounds of formula

[structure: X-substituted phenyl-C(R₂)=N-N(R₃)-C(=N-)(pyrimidine with R₄, R₅)]

| Comp. No. | X | R₂ | R₃ | R₄ | R₅ | physical constant |
|---|---|---|---|---|---|---|
| 5.1 | CH₃ | phenyl | CH₃ | cyclopropyl | CH₃ | |
| 5.2 | H | phenyl | CH₂CH₃ | cyclopropyl | CH₃ | $n_D^{25}$: 1.6145 |
| 5.3 | H | CH₂-phenyl | COCHCl₂ | cyclopropyl | CH₃ | |
| 5.4 | Cl | cyclopropyl | CH₂CH₃ | CH₂OCH₃ | CH₃ | |
| 5.5 | CH₃ | phenyl | CH₃ | C≡C—CH₃ | CH₃ | |
| 5.6 | CH₃ | CF₃ | COCH₂OCH₃ | cyclopropyl | CH₃ | |

TABLE 5-continued

Compounds of formula

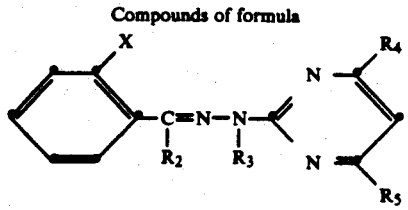

| Comp. No. | X | $R_2$ | $R_3$ | $R_4$ | $R_5$ | physical constant |
|---|---|---|---|---|---|---|
| 5.7 | $CH_3$ | $CH_2CH_3$ | $CH_3$ | cyclopropyl | $CH_3$ | |
| 5.8 | $CH_3$ | $CH_2CH_3$ | $COCHCl_2$ | cyclopropyl | $CH_3$ | |
| 5.9 | Cl | $CH_2CF_3$ | $CH_2CH_3$ | cyclopropyl | $CH_3$ | |
| 5.10 | $CH_3$ | phenyl | $COCHCl_2$ | cyclopropyl | $CH_3$ | | and also the following compounds

| | physical constant |
|---|---|
| 2,4-dimethylphenyl-C(CH$_3$)=N-NH-pyrimidine with CH$_2$OCH$_3$ and Cl substituents | E-Form: m.p. 144–145° C. |
| 2-methylphenyl-C(CH$_3$)=N-NH-pyrimidine with cyclopropyl and CF$_3$ substituents | E-Form: m.p. 104° C.<br>Z-Form: $n_D^{50}$: 1.5484 |
| 2-OCHF$_2$-phenyl-C(CH$_3$)=N-NH-pyrimidine with CH$_2$OCH$_3$ and OCH$_3$ substituents | E-Form: m.p. 123–124° C.<br>Z-Form: m.p. 111–113° C. |

2. FORMULATION EXAMPLES FOR LIQUID ACTIVE INGREDIENTS OF FORMULA I (throughout, percentages are by weight)

2.1. Emulsifiable concentrates

|  | (a) | (b) | (c) |
|---|---|---|---|
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

2.2. Solutions

|  | (a) | (b) | (c) | (d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

2.3. Granulates

|  | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

2.4. Dusts

|  | (a) | (b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA I (throughout, percentages are by weight)

2.5. Wettable powders

|  | (a) | (b) | (c) |
|---|---|---|---|
| a compound of Table 1 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

2.6. Emulsifiable concentrate

| a compound of Table 1 | 10% |
|---|---|
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

2.7. Dusts

|  | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carrier and grinding the mixture in a suitable mill.

2.8. Extruder granulate

| a compound of Table 1 | 10% |
|---|---|
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

2.9. Coated granulate

| a compound of Table 1 | 3% |
|---|---|
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this matter.

2.10. Suspension concentrate

| a compound of Table 1 | 40% |
|---|---|
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

EXAMPLE 3.1

Action against Phytophthora on tomato plants (a) Residual protective action

After a cultivation period of 3 weeks, tomato plants are sprayed with a spray mixture (0.02% active ingredient) prepared from a wettable powder formulation of the test compound. After 24 hours the treated plants are infected with a sporangia suspension of the fungus. Evaluation of the fungus attack is made after the infected plants have been incubated for 5 days at 90–100% relative humidity and 20° C.

(b) Residual curative action

After a cultivation period of 3 weeks, tomato plants are infected with a sporangia suspension of the fungus. After incubation for 22 hours in a humidity chamber at 90–100% relative humidity and 20° C., the infected plants are dried and sprayed with a spray mixture (0.02% active ingredient) prepared from a wettable powder formulation of the test compound. After the spray-coating has dried, the treated plants are replaced in the humidity chamber. Evaluation of the fungus attack is made 5 days after infection.

(c) Systemic action

After a cultivation period of 3 weeks, tomato plants are watered with a spray mixture (0.006% active ingredient, based on the volume of the soil) prepared from a wettable powder formulation of the test compound. Care is taken that the spray mixture does not come into contact with the parts of the plants above the soil. The treated plants are infected 48 hours later with a sporangia suspension of the fungus. Evaluation of the fungus attack is made after the infected plants have been incubated for 5 days at 90–100% relative humidity and 20° C.

Compounds of the Tables exhibit good activity against Phytophthora attack (attack 20% or less). For example, compounds 1.1, 1.5, 1.9, 1.13, 2.1, 2.2, 2.16 and 2.19 reduce Phytophthora attack to 0 to 5%. On the other hand, Phytophthora attack is 100% on untreated and infected control plants.

EXAMPLE 3.2

Action against Plasmopara viticola on vines Residual protective action

Vine seedlings in the 4–5 leaf stage are sprayed with a spray mixture (0.02% active ingredient) prepared from a wettable powder formulation of the test compound. After 24 hours the treated plants are infected with a sporangia suspension of the fungus. Fungus attack is evaluated after incubation for 6 days at 95–100% relative humidity and 20° C.

Compounds of the Tables exhibit good activity against Plasmopara (fungus attack less than 20%). For example, compounds 1.35 and 1.39 reduce Plasmopara attack to 0 to 5%. On the other hand, Plasmopara attack is 100% on untreated and infected control plants.

EXAMPLE 3.3

Action against Cercospora arachidicola on groundnut plants Residual protective action Groundnut plants 10–15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then placed in a greenhouse until the typical leaf specks occur. Evaluation of the fungicidal action is made 12 days after infection and is based on the number and size of the specks.

Compounds of the Tables exhibit good activity against Cercospora (fungus attack less than 20%). For example, compounds 1.1, 1.2, 1.9, 1.11, 1.13, 1.35, 1.45, 1.46, 1.50, 1.166, 2.1, 2.2, 2.9, 2.17 and 2.18 reduce Cercospora attack to 0 to 5%. On the other hand, Cercospora attack is 100% on untreated and infected control plants.

EXAMPLE 3.4

Action against Botrytis cinerea on apples Residual protective action

Artificially damaged apples are treated by dripping onto the damaged areas a spray mixture (0.02% active ingredient) prepared from a wettable powder formulation of the test compound. The treated fruits are then inoculated with a spore suspension of the fungus and incubated for one week at high humidity and about 20° C. Evaluation of the fungicidal action of the test compound is made by counting the number of damaged areas that have rotted.

Compounds of the Tables exhibit good activity against Botrytis. On the other hand, fungus attack is 100% on untreated and infected control plants.

Compounds of the Tables exhibit good activity against Botrytis. For example, compounds 1.2, 1.11, 1.13, 1.35, 1.45, 1.125, 1.157, 1.166, 2.1 and 3.7 reduce Botrytis attack to 0 to 5%. On the other hand, Botrytis attack is 100% on untreated and infected control plants.

EXAMPLE 3.5

Action against Rhizoctonia solani (soil fungus on rice plants)

(a) Protective local soil application 12-day old rice plants are watered with a spray mixture (0.006% active ingredient) prepared from a test compound formulation, without contaminating the parts of the plant above the soil. In order to infect the treated plants, a suspension of mycelia and sclerotia of R. solani is applied to the surface of the soil. Evaluation of the fungus attack on the sheath, leaves and stems is made after incubation for 6 days at 27° C. (day) and 23° C. (night) and 100% relative humidity (humidity chamber) in a climatic chamber.

(b) Protective local foliar application 12-day old rice plants are sprayed with a spray mixture (0.02% active ingredient) prepared from a test compound formulation. One day later the treated plants are infected with a suspension of mycelia and sclerotia of R. solani. Evaluation of the fungus attack on the sheath, leaves and stems is made after incubation for 6 days at 27° C. (day) and 23° C. (night) and 100% relative humidity (humidity chamber) in a climatic chamber.

Compounds of the Tables exhibit good activity against Rhizoctonia. For example, compounds 1.1, 1.9, 1.31, 1.35, 1.45, 1.50, 1.166, 2.1, 2.20, 2.21 and 3.12 reduce Rhizoctonia attack to 0 to 5%. On the other hand, attack is 100% on untreated and infected control plants.

EXAMPLE 3.6

Action against Pyricularia oryzae on rice plants (a) Residual protective action

After a cultivation period of 2 weeks, rice plants are sprayed with a spray mixture (0.02% active ingredient) prepared from a wettable powder formulation of the test compound. After 48 hours the treated plants are infected with a conidia suspension of the fungus. Evaluation of the fungus attack is made after incubation for 5 days at 95-100% relative humidity and 24° C.

(b) Systemic action

Two-week old rice plants growing in pots are watered with a spray mixture (0.006% active ingredient, based on the volume of the soil) prepared from a wettable powder formulation of the test compound. The pots are then filled up with water until the lowermost parts of the stem of the rice plants are standing in water. 48 hours later the treated rice plants are infected with a conidia suspension of the fungus. Evaluation of the fungus attack is made after the infected plants have been incubated for 5 days at 95-100% relative humidity and about 24°.

(c) Curative action

After a cultivation period of 2 weeks, rice plants are infected with a conidia suspension of the fungus. After incubation for 1 to 2 days at 95-100% relative humidity and 24° C. the plants are sprayed with a spray mixture (0.02% active ingredient) prepared from a wettable powder formulation of the test compound. Evaluation of the fungus attack is made after incubation for a further 5 days at 95-100% relative humidity and 24° C.

Compounds of the Tables exhibit a long-lasting action against Pyricularia fungus (less than 20% attack). For example, compounds 1.1, 1.9, 1.46, 2.1, 2.10 and 2.18 reduce Pyricularia attack to 0 to 5%. On the other hand, attack is 100% on untreated and infected control plants.

EXAMPLE 3.7

Action against Helminthosporium gramineum

Wheat grains are contaminated with a spore suspension of the fungus and dried. The contaminated grains are dressed with a suspension of the test compound (600 ppm of active ingredient, based on the weight of the seeds) prepared from a wettable powder formulation. Two days later the grains are placed in suitable agar dishes and after a further 4 days the development of the fungus colonies around the grains is evaluated. Evaluation of the test compound is made on the basis of the number and size of the fungus colonies. The compounds of the Tables inhibit fungus attack substantially (less than 20% attack). For example, compounds 1.1, 1.9, 1.45, 1.46, 1.66 and 2.17 reduce Helminthosporium attack to 0 to 5%. On the other hand, attack is 100% on untreated and infected control seeds.

EXAMPLE 3.8

Action against Fusarium nivale

Wheat grains are contaminated with a spore suspension of the fungus and dried. The contaminated grains are dressed with a suspension of the test compound (600 ppm of active ingredient, based on the weight of the seeds) prepared from a wettable powder formulation. Two days later the grains are placed in suitable agar dishes and after a further 4 days the development of the fungus colonies around the grains is evaluated. Evaluation of the test compound is made on the basis of the number and size of the fungus colonies.

In the case of grains that have been treated with a wettable powder formulation containing a compound of the Tables as active ingredient, the development of fungus colonies is inhibited substantially (less than 20% attack). For example, compounds 1.1, 1.9 and 1.45 reduce Fusarium attack to 0 to 10%. On the other hand, attack is 100% on untreated and infected control seeds.

What is claimed is:

1. A compound of formula I

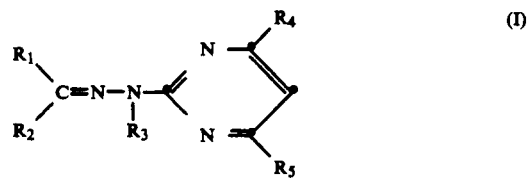

wherein $R_1$ is phenyl, naphthyl, phenyl substituted from one to five times by $R_6$, or naphthyl substituted from one to five times by $R_6$; $R_2$ is $C_1$-$C_6$alkyl, $C_1$-$C_6$alkyl substituted at least once by halogen, $C_1$-$C_3$alkoxy or by $C_3$-$C_6$cycloalkyl, $C_3$-$C_6$cycloalkyl, $C_1$-$C_4$alkoxycarbonyl, phenyl, phenyl mono- to tri-substituted by halogen, $C_1$-$C_3$alkoxy by $C_1$-$C_3$alkyl, benzyl, or benzyl mono- to tri-substituted by halogen, $C_1$-$C_3$alkoxy or by $C_1$-$C_3$alkyl; $R_3$ is hydrogen, $C_1$-$C_6$alkyl or the radical CO-$R_7$; $R_4$ is $C_3$-$C_6$cycloalkyl or $C_3$-$C_6$cycloalkyl mono- to trisubstituted by halogen or by methyl; $R_5$ is hydrogen, $C_1$-$C_6$alkyl, $C_1$-$C_6$alkyl substituted at least once by halogen, hydroxy, cyano or by $C_1$-$C_3$alkoxy, $R_5$ is also $C_3$-$C_5$alkenyl, halogen, hydroxy, $C_1$-$C_3$alkoxy, $C_1$-$C_3$haloalkoxy, $C_3$-$C_6$cycloalkyl or $C_1$-$C_3$alkylthio; $R_6$, independently of any other, is $C_1$-$C_6$alkyl, $C_1$-$C_3$alkyl substituted by $C_1$-$C_3$alkoxy, or $C_1$-$C_4$alkoxy, $C_1$-$C_3$haloalkyl, $C_1$-$C_3$haloalkoxy, halogen, cyano, nitro, hydroxy or the radical $S(O)_n$-$C_1$-$C_4$alkyl; $R_7$ is $C_1$-$C_6$alkyl, or $C_1$-$C_6$alkyl substituted at least once by halogen or by $C_1$-$C_3$alkoxy; and n is 0, 1 or 2; including the acid addition compounds and the metal salt complexes thereof.

2. A compound of formula I according to claim 1 wherein: $R_1$ is phenyl, naphthyl, phenyl substituted up to five times by $R_6$, or naphthyl substituted up to five times by $R_6$; $R_2$ is $C_1$-$C_6$alkyl, $C_1$-$C_6$alkyl substituted from one to five times by halogen or once or twice by $C_1$-$C_3$alkoxy or once by $C_3$-$C_6$cycloalkyl, $C_3$-$C_6$cycloalkyl, phenyl, phenyl mono- to tri-substituted by halogen, $C_1$-$C_3$alkoxy or by $C_1$-$C_3$alkyl, benzyl, or benzyl mono- to tri-substituted by halogen, $C_1$-$C_3$alkoxy or by $C_1$-$C_3$alkyl; $R_3$ is hydrogen, $C_1$-$C_3$alkyl or the radical CO-$R_7$; $R_4$ is $C_3$-$C_6$cycloalkyl or $C_3$-$C_6$cycloalkyl mono- to tri-substituted by halogen and/or by methyl; $R_5$ is hydrogen, $C_1$-$C_6$alkyl, $C_1$-$C_6$alkyl substituted at least once by halogen, hydroxy, cyano or by $C_1$-$C_3$alkoxy, $R_5$ is also $C_3$-$C_5$alkenyl, halogen, hydroxy, $C_1$-$C_3$alkoxy, $C_1$-$C_3$haloalkoxy, $C_3$-$C_6$cycloalkyl or $C_1$-$C_3$alkylthio; $R_6$, independently of any other, is $C_1$-$C_4$alkyl, $C_1$-$C_3$alkoxy, $C_1$-$C_3$haloalkyl, $C_1$-$C_3$haloalkoxy, halogen, nitro or the radical $S(O)_n$-$C_1$-$C_3$alkyl; $R_7$ is $C_1$-$C_6$alkyl, or $C_1$-$C_6$alkyl substituted at least once by halogen or by $C_1$-$C_3$alkoxy; and n is 0, 1 or 2.

3. A compound of formula I according to claim 1 wherein: $R_1$ is phenyl, naphthyl, phenyl substituted up to 5 times by $R_6$, or naphthyl substituted up to 3 times by $R_6$; $R_2$ is $C_1-C_6$alkyl, $C_1-C_6$alkyl substituted from 1 to 5 times by halogen or once or twice by $C_1-C_3$alkoxy or once by $C_3-C_6$cycloalkyl, $C_3-C_6$cycloalkyl, phenyl, phenyl mono- to tri-substituted by halogen, $C_1-C_3$alkoxy and/or by $C_1-C_3$alkyl, benzyl, or benzyl mono- to tri-substituted by halogen, $C_1-C_3$alkoxy or by $C_1-C_3$alkyl; $R_3$ is hydrogen, $C_1-C_3$alkyl or the radical $CO-R_7$; $R_4$ is $C_3-C_6$cycloalkyl, $C_3-C_6$cycloalkyl mono- to tri-substituted by halogen or by methyl or; $R_5$ is hydrogen, $C_1-C_6$alkyl, $C_1-C_6$alkyl substituted at least once by halogen, hydroxy, cyano or by $C_1-C_3$alkoxy, $R_5$ is also $C_3-C_5$alkenyl, halogen, hydroxy, $C_1-C_3$alkoxy, $C_1-C_3$haloalkoxy, $C_3-C_6$cycloalkyl or $C_1-C_3$alkylthio; $R_6$, independently of any other, is $C_1-C_4$alkyl, $C_1-C_3$alkoxy, $C_1-C_3$haloalkyl, $C_1-C_3$haloalkoxy, halogen, nitro or the radical $S(O)_n-C_1-C_3$alkyl; $R_7$ is $C_1-C_6$alkyl, or $C_1-C_6$alkyl substituted at least once by halogen or by $C_1-C_3$alkoxy; and n is 0, 1 or 2.

4. A compound of formula I according to claim 1 wherein: $R_1$ is phenyl, naphthyl, phenyl substituted up to 3 times by $R_6$, or naphthyl substituted up to 3 times by $R_6$; $R_2$ is $C_1-C_6$alkyl, $C_1-C_6$alkyl monosubstituted by $C_1-C_3$alkoxy or $C_3-C_6$cycloalkyl or mono- to tri-substituted by halogen, or $C_3-C_6$cycloalkyl, phenyl, phenyl mono- to tri-substituted by halogen or by $C_1-C_3$alkyl, benzyl, or benzyl mono- to tri-substituted by halogen or by $C_1-C_3$alkyl; $R_3$ is hydrogen or the radical $CO-R_7$; $R_4$ is $C_3-C_6$cycloalkyl or $C_3-C_6$cycloalkyl mono- to tri-substituted by halogen or by methyl; $R_5$ is $C_1-C_6$alkyl, $C_1-C_6$alkyl substituted by hydroxy or $C_1-C_3$alkoxy or at least once by halogen, $R_5$ is also $C_3-C_5$alkenyl, halogen, hydroxy, $C_1-C_3$alkoxy, $C_1-C_3$haloalkoxy, $C_3-C_6$cycloalkyl or $C_1-C_3$alkylthio; $R_6$, independently of any other, is $C_1-C_4$alkyl, $C_1-C_2$alkoxy, $C_1-C_2$haloalkoxy or halogen; $R_7$ is $C_1-C_4$alkyl, or $C_1-C_4$alkyl substituted at least once by halogen.

5. A compound of formula I according to claim 1 wherein: $R_1$ is phenyl substituted up to 3 times by $R_6$ with the proviso that at least the ortho-position in the phenyl ring is substituted; $R_2$ is $C_1-C_3$alkyl; $R_3$ is hydrogen; $R_4$ is $C_3-C_6$cycloalkyl or $C_3-C_6$cycloalkyl substituted by $CH_3$; $R_5$ is $C_1-C_3$alkyl, $C_1-C_3$alkyl substituted by halogen, $R_5$ is also $C_3-C_5$alkenyl, $C_3-C_5$cycloalkyl or $C_1-C_3$alkylthio; $R_6$, independently of any other, is $C_1-C_4$alkyl, halogen or $C_1-C_4$haloalkyl.

6. A compound of formula I according to claim 1 wherein: $R_1$ is α-naphthyl, 2-substituted α-naphthyl, 2,3-disubstituted or 2,4-disubstituted α-naphthyl, wherein the substituents in the 2- and 4-positions can be $C_1-C_3$alkyl, halogen or nitro and the substituent in the 3-position is $C_1-C_3$alkyl; $R_2$ is $C_1-C_3$alkyl; $R_3$ is hydrogen; $R_4$ is $C_3-C_6$cycloalkyl or $C_3-C_6$cycloalkyl substituted by $CH_3$; $R_5$ is $C_1-C_3$alkyl, $C_1-C_3$alkyl substituted by halogen, $R_5$ is also $C_3-C_5$alkenyl, $C_3-C_5$cycloalkyl or $C_1-C_3$alkylthio.

7. A compound of formula I according to claim 6 wherein: $R_1$ is α-naphthyl, 2-methyl-α-naphthyl, 2-methyl-4-nitro-α-naphthyl, 2,4- dimethyl-α-naphthyl, 2,3-dimethyl-α-naphthyl or 4-methyl-α-naphthyl.

8. A compound of the formula I according to claim 1 selected from: 4-methyl-6-cyclopropyl-2-[1-(2-methylphenyl)-ethylidenehydrazino]pyrimidine; 4-methyl-6-cyclopropyl-2-[1-(2-chlorophenyl) ethylidenehydrazino]-pyrimidine; 4-fluoromethyl-6-cyclopropyl-2-[1-(2-methylphenyl) -ethylidenehydrazino]-pyrimidine; 4-methyl-6-cyclopropyl-2-[1-(2,4-dimethylphenyl) -ethylidenehydrazino]-pyrimidine; 4-methyl-6-cyclopropyl-2-[1-(2-methyl-α-naphthyl) -ethylidenehydrazino]-pyrimidine (Compound No. 3.25); 4-methyl-6-cyclopropyl-2-[1-(2,4-dimethyl-α-naphthyl)-ethylidenehydrazino]-pyrimidine (Compound No. 3.26); 4-methyl-6-cyclopropyl-2-[1-(2,5-dimethylphenyl)-ethylidenehydrazino]-pyrimidine (Compound No. 1.35); 4-methyl-6-cyclopropyl-2-[1-(2-bromophenyl) -ethylidenehydrazino]-pyrimidine (Compound No. 1.45).

9. A composition for controlling or preventing attacks by destructive microorganisms, which composition contains as active ingredient at least one compound of formula I according to claim 1 together with a suitable carrier.

10. A composition according to claim 9, which contains as active ingredient at least one compound of formula I in claim 2.

11. A composition according to claim 9, which contains as active ingredient at least one compound of formula I in claim 3.

12. A composition according to claim 9, which contains as active ingredient at least one compound of formula I in claim 4.

13. A composition according to claim 9, which contains as active ingredient at least one compound of formula I in claim 5.

14. A composition according to claim 9, which contains as active ingredient at least one compound of formula I in claim 6.

15. A composition according to claim 9, which contains as active ingredient at least one compound of formula I in claim 7.

16. A composition according to claim 9, which contains as active ingredient at least one compound of formula I in claim 8.

17. A method of controlling or preventing attacks on cultivated plants by phytopathogenic microorganisms, which method comprises applying to the plant, parts of the plant or the locus thereof, as active ingredient, a compound of formula I according to claim 1.

18. A method according to claim 17, which comprises applying as active ingredient a compound according to claim 8.

19. A method according to claim 17, which comprises controlling phytopathogenic fungi.

20. A compound of claim 1 wherein $R_4$ is $C_3-C_6$-cycloalkyl.

21. A compound of claim 20 wherein $R_4$ is cyclopropyl.

* * * * *